United States Patent [19]

Donaldson

[11] 4,258,251
[45] Mar. 24, 1981

[54] APPARATUS FOR USE IN ORDERING TRIALS

[75] Inventor: Gordon B. Donaldson, Glasgow, Scotland

[73] Assignee: University of Strathclyde, Glasgow, Scotland

[21] Appl. No.: 28,912

[22] Filed: Apr. 10, 1979

Related U.S. Application Data

[63] Continuation-in-part of Ser. No. 17,563, Mar. 5, 1979, abandoned, which is a continuation of Ser. No. 811,838, Jun. 28, 1977, abandoned.

[30] Foreign Application Priority Data

Jun. 29, 1976 [GB] United Kingdom ............... 27006/76

[51] Int. Cl.³ .............................................. G06M 3/08
[52] U.S. Cl. ........................... 235/92 AC; 235/92 MS; 434/81; 434/362
[58] Field of Search ........ 235/92 ST, 92 MS, 92 AC, 235/92 CT; 35/22 A, 22 R

[56] References Cited

U.S. PATENT DOCUMENTS

| | | | |
|---|---|---|---|
| 3,660,645 | 5/1972 | Lecht et al. | 235/92 AC |
| 3,665,165 | 5/1972 | Strandberg et al. | 235/92 T |
| 3,783,257 | 1/1974 | Friedman et al. | 235/92 ST |

*Primary Examiner*—Joseph M. Thesz
*Attorney, Agent, or Firm*—Mason, Fenwick & Lawrence

[57] ABSTRACT

Apparatus for conducting Ordering Trials including a set of counters each incorporating an electrical circuit element which covertly identifies that counter and a box having locations for receipt of the counters. The counters and locations are fitted with plugs and sockets which are interengageable and permit the circuit element to be connected to electrical read-out circuitry which includes circuitry for identifying which counter is in which location. An arithmetic unit operating according to a predetermined algorithm is connected to the output of the interrogation circuitry to provide a measure of the result of a trial.

7 Claims, 8 Drawing Figures

APPARATUS FOR USE IN ORDERING TRIALS

This application is a continuation-in-part of my earlier application Ser. No. 17,563 filed Mar. 5, 1979, now abandoned, which was a continuation of my earlier application Ser. No. 811,838 filed June 28, 1977, also now abandoned.

This invention relates to apparatus for use in conducting and in assessing the results from Ordering Trials undertaken by a subject.

Ordering Trials are well known and they usually require the subject to arrange in sequence a set of objects respectively having unique characteristics. Thus, for example, where the unique characteristic is colour tone or hue the requirement of the Trial is to arrange different colour tones or hues in order. The 100-hue test introduced by Farnsworth and described in J.O.S.A. volume 33 page 568 (published 1943) operates on this basis and has found a wide and continuing use in both clinical and research practice in relation to colour vision deficiencies.

In order to measure the result of a Trial, scoring systems have been evolved which rely upon the aggregation of errors caused by incorrectly ordering each object in relation to its neighbouring objects or in relation to its true location. Hitherto scoring according to these scoring systems has had to be undertaken manually utilising numbers printed on each object at a location hidden from the view of the subject. This has meant that measuring the result of the trial has been tedious and very time consuming to such an extent that it has effectively precluded a subject from repeatedly undertaking the same Trial, whereby statistically more accurate information might be derived from the set of Trials.

It is an object of the present invention to provide apparatus for use in conducting Ordering Trials which permits simplification in measuring the Trial result.

According to the present invention there is provided apparatus for use in conducting Ordering Trials, wherein a set of counters respectively having unique characteristics, the sequential ordering of which is to be undertaken by a subject, are provided, with each counter including at least one electrical circuit element, the electrical characteristic of which uniquely identifies that counter, and a holder is provided having a set of identical locations respectively for receiving one of the counters. The holder includes a plurality of electrical conductors associated respectively with those locations, and interengageable electrical terminals are provided at the locations and on the counters so that when a particular location receives a particular counter the electrical circuit element of that counter is connected electrically to the pertaining electrical conductors. Read-out means are connected to the electrical conductors and incorporate interrogation circuitry which is operable to determine the electrical characteristics of the counters in the respective locations and an arithmetic unit operating according to a predetermined algorithm is connected to the output of the interrogation circuitry to provide a measure of the result of a trial.

An embodiment of the present invention will now be described, by way of example, with reference to the accompanying drawings, in which.

Figure 4:
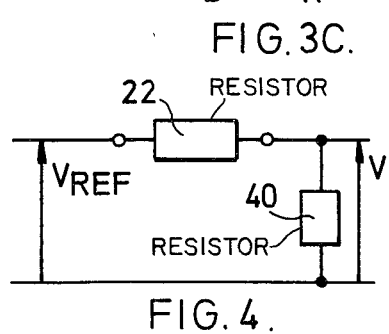

FIGS. 3A to D illustrate alternative electrical circuit configurations of a detail of the apparatus;

FIG. 4 is a circuit diagram of another detail; and

Figure 1:
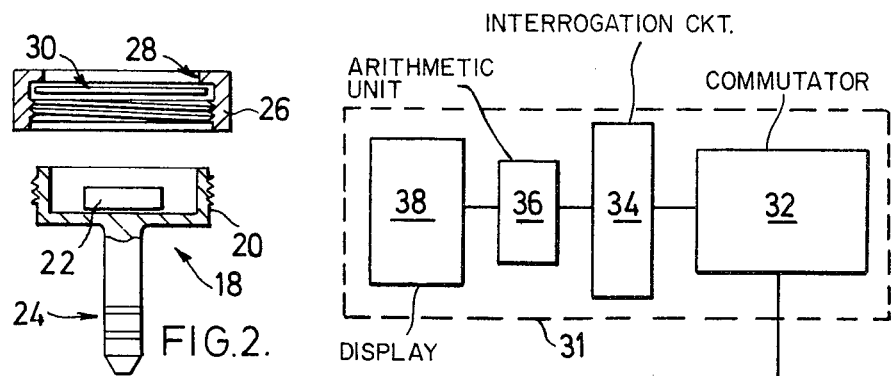
FIG. 1 shows a perspective view of the box-like holder with parts shown in section, and the electrical circuit associated therewith shown in block diagram form.
Figure 5:
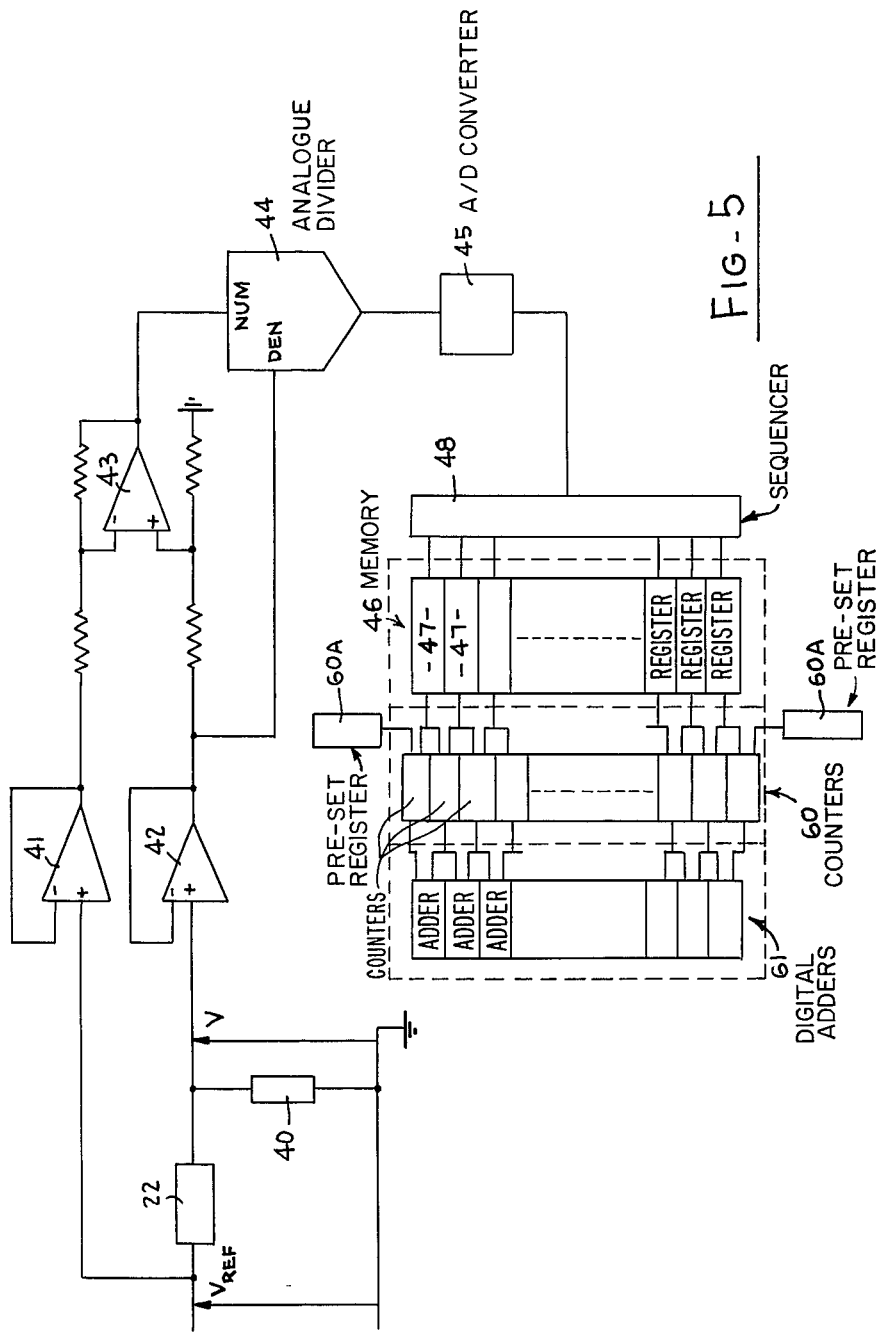

FIG. 5 illustrates components of the arithmetic unit of FIG. 1.

Figure 2:
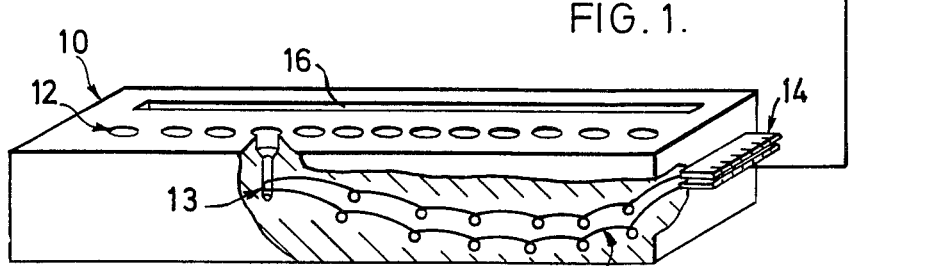
FIG. 2 is an exploded view of one of the counters with parts shown in side elevation and parts in section to reveal the construction thereof.

In order to conduct a colour-vision Ordering Trial the present embodiment provides a box 10 having a plurality of sockets 12 arranged in a row, these sockets 12 incorporating electrical connectors 13 which are coupled by way of electrical conductors 15 to a terminal block 14 at one end of the box 10. Within the box 10 and temporarily stored in a storage recess 16 is a set of counters 18 which are individually movable from the recess 16 to any one of the sockets 12. For this purpose each counter 18 is as shown in FIG. 2, i.e. comprising a cup-shaped member 20 within which is located an electrical circuit element 22 electrically-connected to a Jack plug 24 mounted on the base of the member 20. The Jack plug 24 is dimensioned to fit each of the sockets 12. The member 20 is externally screw-threaded and receives a screw-threaded cap 26 which is apertured at 28 and acts as a frame and clamp to secure a coloured disc 30 to the member 20. Each cap 26 is made of black plastics and the discs 30 vary in colour from counter to counter. Thus the counters 18 respectively have unique visual characteristics and by virtue of the arrangement of Jack plug and socket 24, 16 the counters 18 can be interchangeably located in the sockets 16 where the electrical connectors 13 and the terminal block 14 permit the nature of the electrical characteristic of each counter (which varies from counter to counter) to be interrogated by a read-out 31.

The read-out 31 includes a commutator 32 whereby each of the electrical connectors 13 is connected in sequence to interrogation circuitry 34 which is operable to determine the electrical characteristic of the elements 22 forming part of the respective counters 18. At the output of the circuitry 34 there is an arithmetic unit 36 which operates (either in analogue or digital mode) according to a predetermined algorithm (as will be explained) to provide a measure of the result of a trial which is displayed in a display unit 38.

The form of the read-out 31 is in part dictated by the form of the circuit element 22 of the counter 18 and in part by the number of counters 18 which determine the degree of discrimination required. Thus, for example the element 22 may take the form of a resistor (R) having a different value in each counter 18. Alternatively, the element 22 may take the form of a parallel combination of resistor (R) and zener diode (Z) the values of each of which differ from counter to counter. Alternatively the element 22 may incorporate resistors (R) and diodes (D) or resistors (R), zeners (Z) and diodes (D), with the diodes connected in parallel circuits with reversed polarity. These alternatives are illustrated in FIGS. 3A-D and in each case the interrogator 34 of the read-out 31 is arranged as shown in FIG. 4 to connect the element 22 in series with a reference element 40, to apply a reference voltage ($V_{REF}$) to the series combination, and to obtain the resultant voltage (V) appearing across the reference element 40.

To illustrate the operation of the circuit shown in FIG. 4 in the simplest case where the element 22 is a single resistor and the reference element 40 is also a single resistor, it follows that $$V = \frac{R_{40} \cdot V_{REF}}{R_{40} + R_{22}}$$

The arithmetic unit 36 which is connected to the interrogator 34 can operate partly on an analogue basis utilising the voltages of FIG. 4 providing an analogue signal which is then digitised. Alternatively, the voltages of FIG. 4 may each be digitisied (for example, by comparison with a staircase waveform) and the arithmetic unit 36 may then operate throughout on a digital basis.

The arithmetic unit 36 identifies the counter concerned by evaluating $R_{22}$ from the information made available to it by the interrogation unit. By way of example and by reference to the simple example discussed in connection with FIG. 4 because $$V = \frac{R_{40} \times V_{REF}}{R_{40} + R_{22}}$$

it follows that $$R_{22} = \frac{R_{40}(V_{REF} - V)}{V}$$

and to implement this the arithmetic unit includes a circuit as shown in FIG. 5 composed of commercially available circuit elements comprising high-impedance unity-gain buffer amplifiers 41, 42 having their inputs connected to sense the voltages $V_{REF}$ and V respectively in FIG. 4, the outputs of these amplifiers are connected to the inputs of a difference amplifier 43 the output of which provides a signal proportional to $V_{REF}$ - V and which is fed into the numerator input of an analogue divider 44 whose denominator input is taken from the output of buffer amplifier 42. The output from the divider 44 is an analogue signal proportional to $$\frac{V_{REF} - V}{V},$$

and since the value of $R_{40}$ is constant this analogue signal is proportional to the value of $R_{22}$. The unity gain and difference amplifiers may conveniently be those produced by National Semiconductors Inc., Catalogue No. LM 741C and the analogue divider may be that sold by Analogue Devices Inc., Catalogue No. AD 532. The amplifiers 41, 42 and 43 of course require to be connected in a manner appropriate to their function, for example as depicted in FIG. 5. Connected to the output of the divider 44 there is an analogue-to-digital converter 45, a memory device 46 composed of a series of registers 47, and a sequencer 48 synchronised with the operation of the commutator 32 of FIG. 1 and arranged to couple the output of converter 45 to the respective registers 47 in turn so that the evaluated $R_{22}$ values may be stored therein.

The individual registers 47 feed into digital counters 60 arranged respectively to subtract the values fed thereto from adjacent registers 47 so that the counters 60 output the 'difference values' referred to previously and adjacent counters 60 feed into digital adders 61 so as to add adjacent differences thereby to evaluate an "error" value for each counter 18 as previously described. The outputs from the adders 61 are fed to the display unit 38 for display in the desired manner. Because there is one more counter 60 than registers 47 the first and last counter 60 each has one input supplied by preset registers 60A.

In a satisfactory embodiment, the A/D converter 45 may produce numbers linearly related to the numbers on the caps 26. For example these digital numbers may be 8 bit numbers. The components operating digitally in FIG. 5 may be of the Texas Instruments 74 series TTL logic range. Thus block 48 may be made up of inverters, buffers, counters, decoders and a sequencer clock controlled by standard 74 series TTL logic, all formed of Texas Instruments 74 series off-the-shelf Integrated Circuit components, as will be well recognised by those skilled in the art. Similarly the registers 47 and 60A may be Texas Instruments 74 series bit registers, the counters 60 may be formed of 74 series inverters, adders and a register and the adders 61 may be 74 series adders and registers all of which are also Texas Instruments 74 series off-the-shelf Integrated Circuits.

The arithmetic unit 36 in addition to evaluating $R_{22}$ also scores the Ordering Trial in accordance with a predetermined algorithm. For example one algorithm commonly used in the Farnsworth Test is to determine an "error value" for each socket 12 by initially evaluating $R_{22}$ for the counter in each socket, computing the numerical difference (scalar) between the thus identified counter values of adjacent sockts, and for each socket, adding adjacent differences. These error values are then displayed in graphical form in the display 38 and are aggregated and displayed as an aggregate error figure for the trial. The graphic part of the display 38, as is conventional is plotted in polar co-ordinates, radial dimension indicating error values and the angular dimension representing the different sockets 12.

Figure 3A:
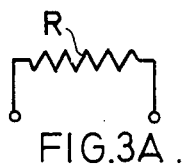
Figure 3B:
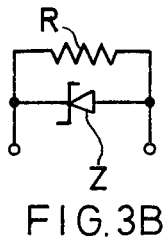

In the case where the element 22 is of the form illustrated in FIG. 3B the value of the element 22 is represented in a two-digit system of which the resistor provides one digit and the zener provides the other digit. The interrogator unit 34 operates in two stages: applying a first reference voltage large enough to turn on the zener of all the counters whereby to give an output that is independent of resistance value but dependent upon individual zener voltage drop: and a second reference voltage low enough to prevent any zeners from conducting whereby to give an output which is independent of zener voltage drop but is dependent on resistance value.

Figure 3C:
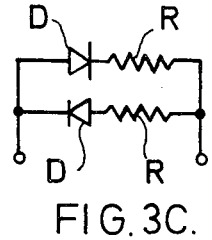
Figure 3D:
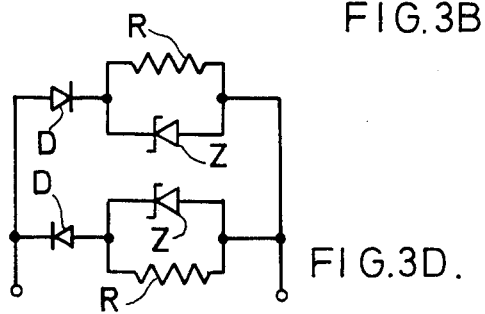

In the case where the element 22 is of the form illustrated in FIG. 3C the value of the element is ascertained as previously described with reference to FIG. 3A but utilising a first reference voltage of say positive polarity and then a second reference voltage of the opposite polarity. Likewise, when the elements 22 are in the form of FIG. 3D the procedure described above in relation to FIG 3B can be utilised with reference voltages of say positive polarity followed by negative polarity reference voltages to evaluate the element.

Because the output of the arithmetic unit 36 operates in digital format its logic circuitry controlling the algorithm of operation can readily be altered in any desired manner. Furthermore the error values and the enumerated values of the counters can be stored in a digital memory system for subsequent use by the display unit 38. This arrangement has the advantage that the scale factor for the polar chart can be determined after completion of all the error values by the arithmetic unit 36 in order that the most advantageous presentation of the information can be effected. Furthermore, although it is preferred to plot socket location in sequence angularly on the chart the display could be arranged to associate error values with counter numbers which would then be displayed angularly in sequence.

The commutator 32 may take any convenient form such as a diode network operated by control logic or it may take the form of a plurality of transistor switches operated sequentially by control logic. Alternatively the commutator 32 may incorporate minaturised reed switches.

The number and shape of the boxes 10 is not important to the present invention. Conveniently however the boxes are four in number each being connected to the read out 31, whereby the coloured discs 30 may be arranged in subgroups one to each box. In an alternative form the sockets 12 are arranged in a closed loop. Although the components 20, 26 of the counters 18 are illustrated as being connected by a screw thread they could, of course, be manufactured to permit connection by a simple push fit.

What is claimed is:

1. Apparatus for use in conducting Ordering Trials, comprising
    a set of counters respectively having unique characteristics the sequential ordering of which is to be undertaken by a subject,
    a holder having a set of identical locations respectively for receiving a said counter,
    each counter comprising at least one electrical circuit element the electrical characteristic of which uniquely identifies that counter, the holder comprising a plurality of electrical conductors associated respectively with said locations, interengageable electrical terminals provided at said locations and on the counters such that when a particular location receives a particular counter the electrical circuit element of that counter is connected electrically to the pertaining electrical conductors, read-out means connected to said electrical conductors, said read-out means incorporating interrogation circuitry which is operable to determine the electrical characteristics of the counters in the respective locations, and an arithmetic unit operating according to a predetermined algorithm and connected to the output of the interrogation circuitry to provide a measure of the result of a trial.

2. Apparatus as claimed in claim 1, wherein said interengageable electrical terminals are in the form of jack plugs and sockets, the jack plugs being mounted on the counters and the sockets forming said locations in the holder.

3. Apparatus as claimed in claim 1, wherein each counter comprises only one electrical circuit element which is in the form of resistance, the resistance value being different for each counter in the set.

4. Apparatus as claimed in claim 1, wherein said interrogation circuitry comprises a reference impedance element connectible in series with said electrical circuit element and with a source of reference voltage.

5. Apparatus as claimed in claim 1, wherein each electrical circuit element is in the form of a resistance in parallel with a zener diode.

6. Apparatus as claimed in claim 1, wherein each electrical circuit element is in the form of a series-connected resistor and diode in parallel with a further series connected resistor and diode, the diodes being connected with opposed polarities.

7. Apparatus as claimed in claim 1, wherein each circuit element is in the form of a parallel-connected resistor and zener diode in series with a diode and a further parallel-connected resistor and zener diode in series with a further diode, the two series circuits being connected in parallel with the diodes having opposed polarities.

* * * * *